(12) United States Patent
Feng et al.

(10) Patent No.: US 9,796,675 B1
(45) Date of Patent: Oct. 24, 2017

(54) INTERMEDIATE FOR SYNTHESIZING PAROXETINE, METHOD FOR PREPARING THE SAME, AND USES THEREOF

(71) Applicant: Zhejiang Jiuzhou Pharmaceutical Co., Ltd., Taizhou (CN)

(72) Inventors: Xiaoming Feng, Taizhou (CN); Yu Zhang, Taizhou (CN); Xiaohua Liu, Taizhou (CN); Qian Yao, Taizhou (CN); Lili Lin, Taizhou (CN); Guoliang Zhu, Taizhou (CN)

(73) Assignee: Zhejiang Jiuzhou Pharmaceutical Co., Ltd, Taizhou Zhejiang (CN)

( * ) Notice: Subject to any disclaimer, the term of this patent is extended or adjusted under 35 U.S.C. 154(b) by 0 days.

(21) Appl. No.: 15/511,244

(22) PCT Filed: Jun. 15, 2015

(86) PCT No.: PCT/CN2015/081422
§ 371 (c)(1),
(2) Date: Mar. 15, 2017

(87) PCT Pub. No.: WO2016/045416
PCT Pub. Date: Mar. 31, 2016

(30) Foreign Application Priority Data

Sep. 22, 2014 (CN) .......................... 2014 1 0486209
Jun. 1, 2015 (CN) .......................... 2015 1 0291876

(51) Int. Cl.
*C07D 211/88* (2006.01)
*C07D 231/12* (2006.01)

(52) U.S. Cl.
CPC .......... *C07D 211/88* (2013.01); *C07D 231/12* (2013.01)

(58) Field of Classification Search
CPC .......................... C07D 211/88; C07D 231/12
See application file for complete search history.

(56) References Cited

PUBLICATIONS

The Journal of Organic Chemistry,vol. 80, No. 11, Apr. 29, 2015, pp. 5704-5712.
Tetrahedron Asymmetry, vol. 22, No. 1, Jan. 31, 2011, pp. 1-3.
Tetrahedron Letters, vol. 38, No. 34, Dec. 31, 1997, p. 5955-5958.

Primary Examiner — Timothy R Rozof

(57) ABSTRACT

A paroxetine intermediate, a method for preparing the same, and uses thereof are provided. Specifically, the method includes: reacting a compound of formula I below with a compound of formula II in the presence of an organic base under the catalysis of a complex formed from a chiral amine oxide L and a rare-earth metal compound $Ln(OTf)_3$ to prepare a compound of formula III below: wherein $R_1$ is alkyl, phenyl or benzyl; $R_2$, $R_3$, $R_4$ are each independently $C_1$-$C_6$ alkyl or $C_6$-$C_{10}$ aryl; the chiral amine oxide L has the following structure: wherein n=1, 2; and R=Ph—, 2,6—$Me_2C_6H_3$—, 2,6—$Et_2C_6H_3$—, 2,6-$iPr_2C_6H_3$—, $Ph_2CH$—.

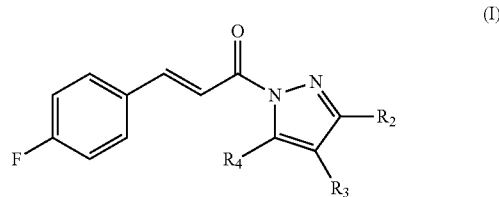

(I)

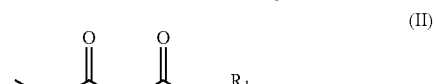

(II)

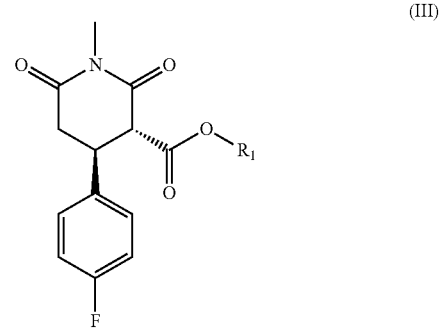

(III)

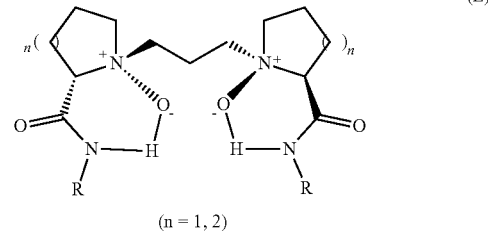

(L)
(n = 1, 2)

10 Claims, 2 Drawing Sheets

INTERMEDIATE FOR SYNTHESIZING PAROXETINE, METHOD FOR PREPARING THE SAME, AND USES THEREOF

FIELD OF THE INVENTION

The invention relates to the technical field of paroxetine, and specifically to an intermediate for paroxetine, a method for preparing the same, and uses thereof.

BACKGROUND OF THE INVENTION

Paroxetine is indicated for treating various types of depression disorders, including depression with anxiety and reactive depression. The chemical name of paroxetine is trans-(-)-3-[(1,3-benzodioxol-5-yl-oxy)methyl]-4-(4-fluorophenyl)piperidine with the following structure:

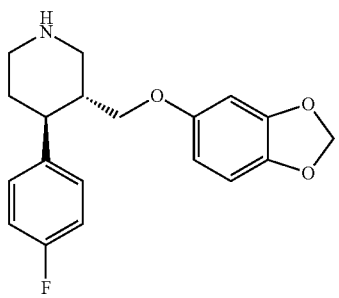 [SMILES: Fc1ccc([C@H]2CCNC[C@@H]2COc2ccc3c(c2)OCO3)cc1]

and a compound of formula III below is an intermediate commonly used for synthesizing paroxetine,

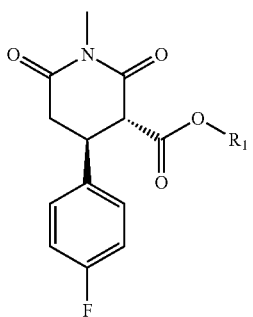

III

Paroxetine can be prepared from the compound of the formula III according to the method provided in WO2009005647 A2, which provides a reaction scheme shown below:

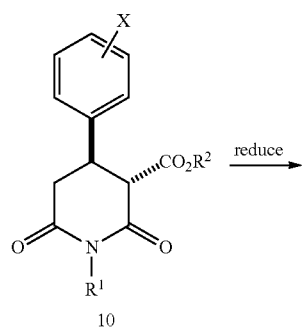

10

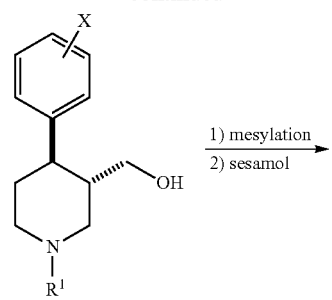

11

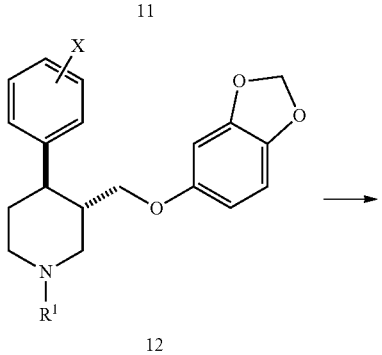

12

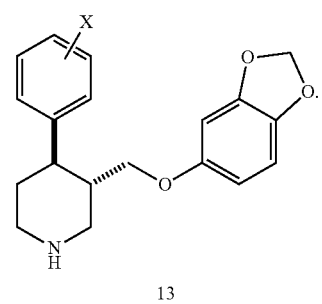

13

The methods for preparing the compound of the formula III as disclosed in the existing literature generally include the following two methods, for example:

The Journal of Fine Chemical Intermediates, 2007, 37(3), P41-44 discloses a method for preparing a racemic compound of the formula III, including reacting ethyl 4-fluorocinnamate with ethyl 3-(methylamino)-3-oxopropanoate to obtain the racemic compound of formula III, and the racemic compound of the formula III needs to be resolved to obtain an optically pure compound of formula III, which has a great loss in raw materials, resulting in an increase of cost.

Tetrahedron: Asymmetry 22 (2011) 1-3 discloses a method as shown below:

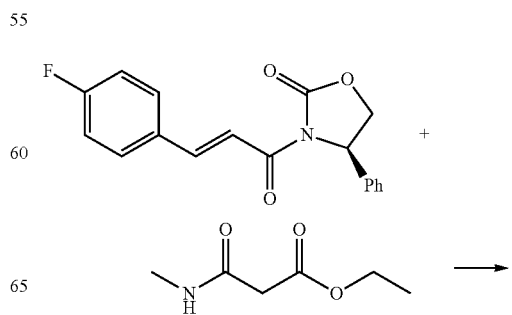

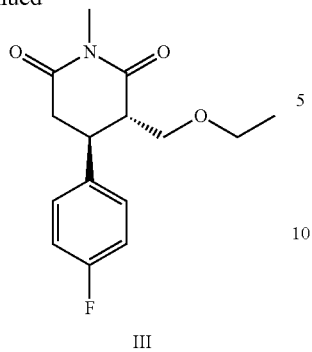

III

In this method, firstly a chiral amide, i.e. (R)-3-(3-(4-fluorophenyl)acryloyl)-4-phenyloxazolidin-2-one is obtained by reacting a chiral auxiliary, i.e., (R)-4-phenyl-2-oxazolinone, with p-fluorocinnamic acid, and then the compound of formula III is obtained through conjugate addition and cyclization between the chiral amide and ethyl 3-(methylamino)-3-oxopropanoate in the presence of sodium hydride. Sodium hydride is inflammable and explosive, requires rigorous reaction conditions, and hence is unfavorable to large-scale industrial production. Moreover, the product obtained through repeating the route by the skilled person according to the method provided in the examples has a poor optical purity and a low yield.

Therefore, there is a need for developing a new synthesis process for preparing the compound of formula III, so as to meet the demand of larger-scale industrial production.

SUMMARY OF THE INVENTION

For purpose of solving the disadvantages that the compound of formula III prepared through the existing route has a poor optical purity and a low yield, and the like, the present invention provides a technical solution as shown below:

A compound of formula I below is provided:

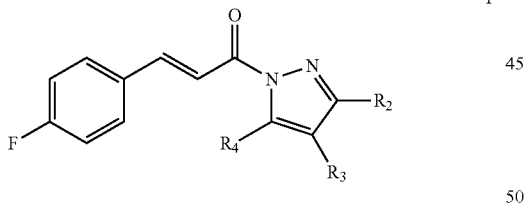

I wherein $R_2$, $R_3$, $R_4$ are each independently hydrogen, $C_1$-$C_6$ alkyl or $C_6$-$C_{10}$ aryl;

preferably $R_2$, $R_3$, $R_4$ are each independently hydrogen, methyl, ethyl, propyl, phenyl, 4-methylphenyl, 3-methylphenyl.

Preferably, the compound of the formula I has a structure selected from the following structures:

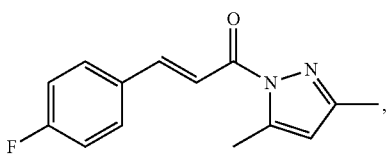

Ia

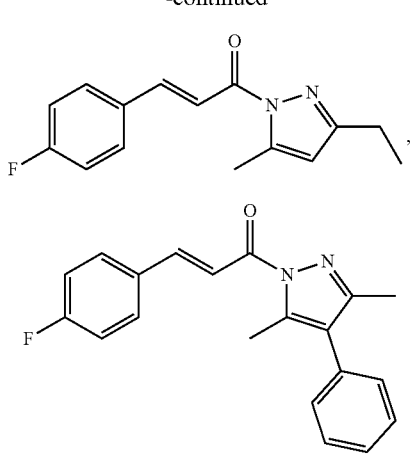

Furthermore, the present invention provides a method of preparing a compound of formula III below,

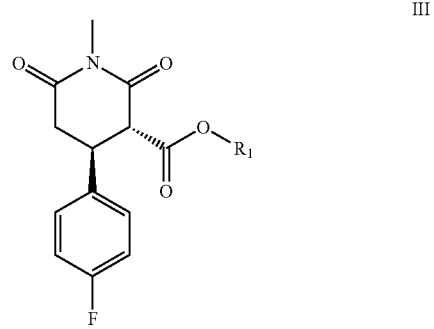

III obtained by reacting a compound of formula I with a compound of formula II in the presence of an organic base under the catalysis of a complex formed from a chiral amine oxide L and a rare-earth metal compound $Ln(OTf)_3$;

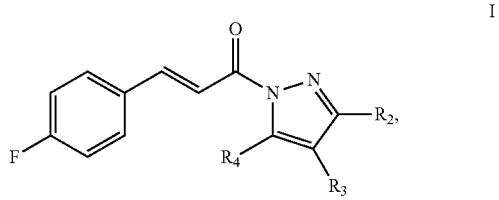

I

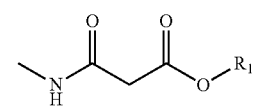

II wherein $R_1$ is alkyl, phenyl or benzyl, preferably $C_1$-$C_6$ alkyl, phenyl or benzyl;

$R_2$, $R_3$, $R_4$ are each independently $C_1$-$C_6$ alkyl or $C_6$-$C_{10}$ aryl.

The chiral amine oxide L has the following structure:

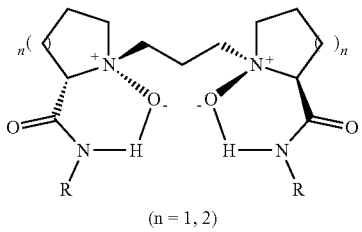

(n = 1, 2)

wherein n=1, 2; and R=Ph—, 2,6—Me$_2$C$_6$H$_3$—, 2,6—Et$_2$C$_6$H$_3$—, Ph$_2$CH—; and preferably, the chiral amine oxide L is L-PiMe$_2$ having the following structure:

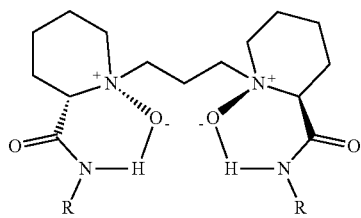

wherein R is 2,6-Me$_2$C$_6$H$_3$.

Ln in the rare-earth metal compound Lu(OTf)$_3$ represents a lanthanide metal, which in particular may be La, Ce, Pr, Nd, Pm, Sm, Eu, Gd, Tb, Dy, Ho, Er, Tm, Yb, Lu.

Preferably the rare-earth metal compound Ln(OTf)$_3$ is gadolinium trifluoromethanesulfonate [Gd(OTf)$_3$], holmium trifluoromethanesulfonate [Ho(OTf)$_3$], ytterbium trifluoromethanesulfonate [Yb(OTf)$_3$], erbium trifluoromethanesulfonate [Er(OTf)$_3$].

The organic base is preferably an amine, and in particular may be triethylamine, diisopropylethylamine, trimethylamine, tri-n-propylamine, tri-n-butylamine, dimethylaniline, diethylaniline, dimethyl benzylamine, diethyl benzylamine, 1,8-diazabicyclo[5.4.0]undec-7-ene (DBU).

The reaction solvent is selected from alkanes, such as pentane, hexane, heptane, etc.; halogenated hydrocarbons, such as dichloroethane, chloroform, etc; aromatic hydrocarbons, such as toluene, ethylbenzene, isopropyl benzene; ethers, such as tetrahydrofuran, methyl tert-butyl ether, 2-methyltetrahydrofuran, etc.; and esters, such as ethyl acetate, isopropyl acetate, etc.; and The reaction temperature is preferably 30-35° C.

The molar ratio of the compound of the formula I to L is preferably 1:(0.005-0.04), and more preferably 1:(0.01-0.03).

The molar ratio of the compound of the formula I to Ln(OTf)$_3$ is preferably 1:(0.005-0.04), and more preferably 1:(0.01-0.03).

The molar ratio of the compound of the formula I to the organic base is preferably 1:(1-4), and more preferably 1:(1-2).

Furthermore, the present invention provides a method for preparing a compound of formula I:

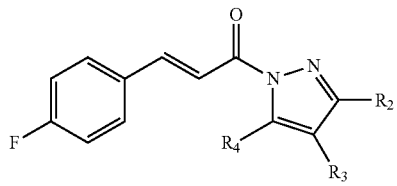

obtained by condensing a compound of formula IV below with p-fluorocinnamic acid in the presence of a dehydrant and an organic base,

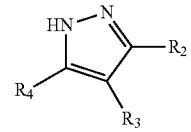

wherein R$_2$, R$_3$, R$_4$ are the same as defined above.

The dehydrant is preferably 1-ethyl-(3-dimethylaminopropyl)carbodiimide hydrochloride (EDCI), 2-(7-azabenzotriazol)-N,N,N',N')-tetramethyluronium hexafluorophosphate (HATU), dicyclohexylcarbodiimide (DCC) benzotriazole-1-yl-oxytripyrrolidinophosphonium hexafluorophosphate (PyBOP), etc.

The organic base is N-methylmorpholine, triethylamine, diisopropylethylamine, trimethylamine, tri-n-propylamine, tri-n-butylamine, dimethylaniline, diethylaniline, dimethyl benzylamine, diethyl benzamine, 1,8-diazabicyclo[5.4.0]undec-7-ene, etc.

The reaction solvent is selected from alkanes, such as pentane, hexane, heptane, etc.; halogenated hydrocarbons, such as dichloroethane, chloroform etc.; aromatic hydrocarbons, such as toluene, ethylbenzene or isopropyl benzene, ethers, such as tetrahydrofuran, methyl tert-butyl ether, 2-methyltetrahydrofuran etc.; and esters, such as ethyl acetate, isopropyl acetate etc., The reaction temperature is 20° C. to reflux temperature, and preferably is 20-30° C.

The molar ratio of the compound of the formula I to the dehydrant is preferably 1:(1-3), and more preferably 1:(1-2).

During the preparation of the compound of the formula I, the molar ratio of the compound of the formula I to the organic base used is 1:(1-3), and more preferably 1:(1-2).

Preferably, in the present invention, the compound of the formula I is prepared through the following scheme:

the compound of the formula IV is condensed with p-fluorocinnamic acid in the presence of the dehydrant and the organic base to obtain a condensation product, which is concentrated and then purified by using an organic solvent to obtain the compound of the formula I.

The solvent used in the purifying process is one of hexane, heptane, petroleum ether, toluene, methyl tert-butyl ether (MTBE), and ethyl acetate or a mixture thereof; and preferably the solvent used for purifying is petroleum ether/ethyl acetate, heptane, hexane/ethyl acetate, heptane/ethyl acetate, toluene, or MTBE.

When the technical solution provided by the present invention is used to prepare the compound of the formula III, the conversion rate of reaction raw materials is high, and a product with a high yield and a high optical purity is obtained simply through a recrystallization procedure. Therefore, the present invention has a very high application value in the industry field.

DETAILED DESCRIPTION

Figure 1:
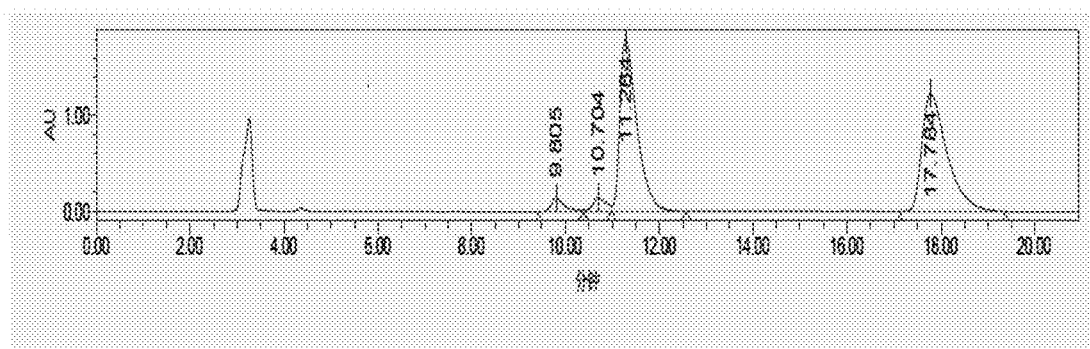
FIG. 1 is an HPLC spectrum of a racemic control liquid of compound IIIa.

In order to understand the disclosure of the present invention better, the present invention is further described hereafter in combination with specific examples, but these specific examples are not intended to limit the disclosure of the present invention.

The compound of the formula I can be prepared according to the following examples:

General Method: Preparation of Compound of Formula I

Into a 250 ml round-bottomed flask were weighed the pyrazole compound IV (30 mmol), and 1-ethyl-(3-dimethylaminopropyl)carbodiimide hydrochloride (EDCI) (30-45 mmol) and N-methylmorpholine (30-45 mmol) sequentially. 100-200 mL of dichloromethane was added to dissolve them, and then p-fluorocinnamic acid (30 mmol) was added slowly to react overnight. The product was washed with water, concentrated to dryness, and then crystallized with petroleum ether/ethyl acetate (or heptane, or hexane/ethyl acetate, or heptane/ethyl acetate, or toluene, or MTBE, etc.) to obtain 21-29 mmol of pure p-fluorocinnamoyl pyrazole compound III with a yield of 70-97%.

The compound of the formula III can be prepared according to the following method:

General Method: Preparation of Compound of Formula III

Into a dry reaction flask were weighed a metal catalyst Ln(OTf)$_3$ (0.01-0.03 mol), a chiral ligand L (0.02 mol), the p-fluorocinnamoyl pyrazole III (0.2 mol) sequentially. The flask was replaced with nitrogen for 3 times. 300 mL of dichloromethane was added to activate at 35° C. for 10-30 min. A monoamide II (0.2 mol) and Et$_3$N (0.2-0.4 mol) were added sequentially to react at 30-50° C. for 40-100 hours, and the reaction solution was washed with dilute hydrochloric acid, concentrated to dryness, and crystallized with petroleum ether/ethyl acetate to obtain 0.016-0.0174 mol of catalysate with a yield of 80-87%.

Preferred Embodiments:

EXAMPLE 1

Preparation of Compound of Formula Ia

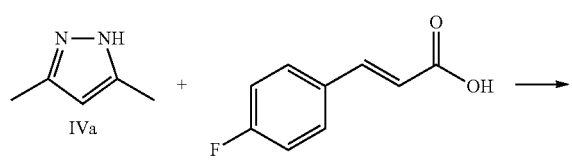

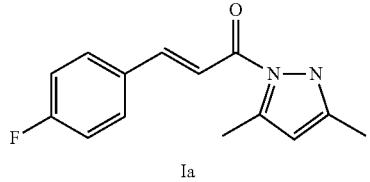

Into a 250 ml round-bottomed flask were weighed pyrazole (30 mmol), 1-ethyl-(3-dimethylaminopropyl)carbodiimide hydrochloride (EDCI) (30 mmol), and N-methylmorpholine (30 mmol) sequentially 100 mL of dichloromethane was added to dissolve them, and then p-fluorocinnamic acid (30 mmol) was added slowly to react overnight. The product was washed with water, concentrated to dryness, and then crystallized with petroleum ether/ethyl acetate to obtain 7.2 g of pure p-fluorocinnamoyl-3,5-dimethylpyrazole with a yield of 97%.

$^1$H-NMR(400 MHz,CDCl3), δ=7.858-7.861 (m,2H), δ=7.646-7.681 (m,2H,), δ=7.074-7.117 (m,2H), δ=6.011 (s,H), δ=2.618 (s,3H), δ=2.287 (s,3H).

ESI-MS (m/z)=244.9[M+H]:

The melting point: 92.5-94.5° C.

EXAMPLE 2

Preparation of Compound of Formula I

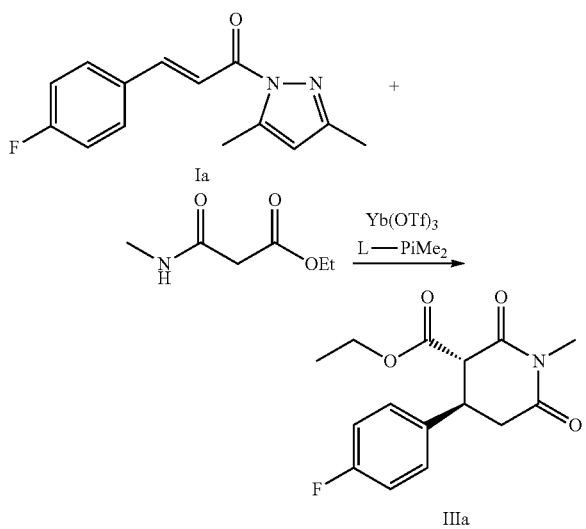

Figure 2:
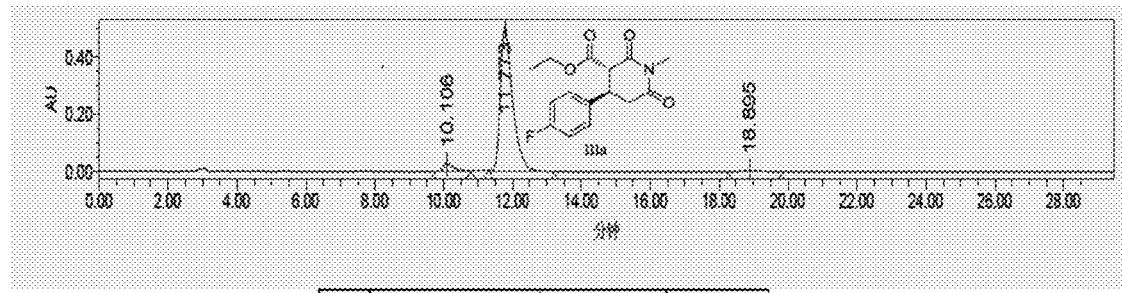
FIG. 2 is an HPLC spectrum of a compound IIIa prepared according to Example 2.
Figure 3:
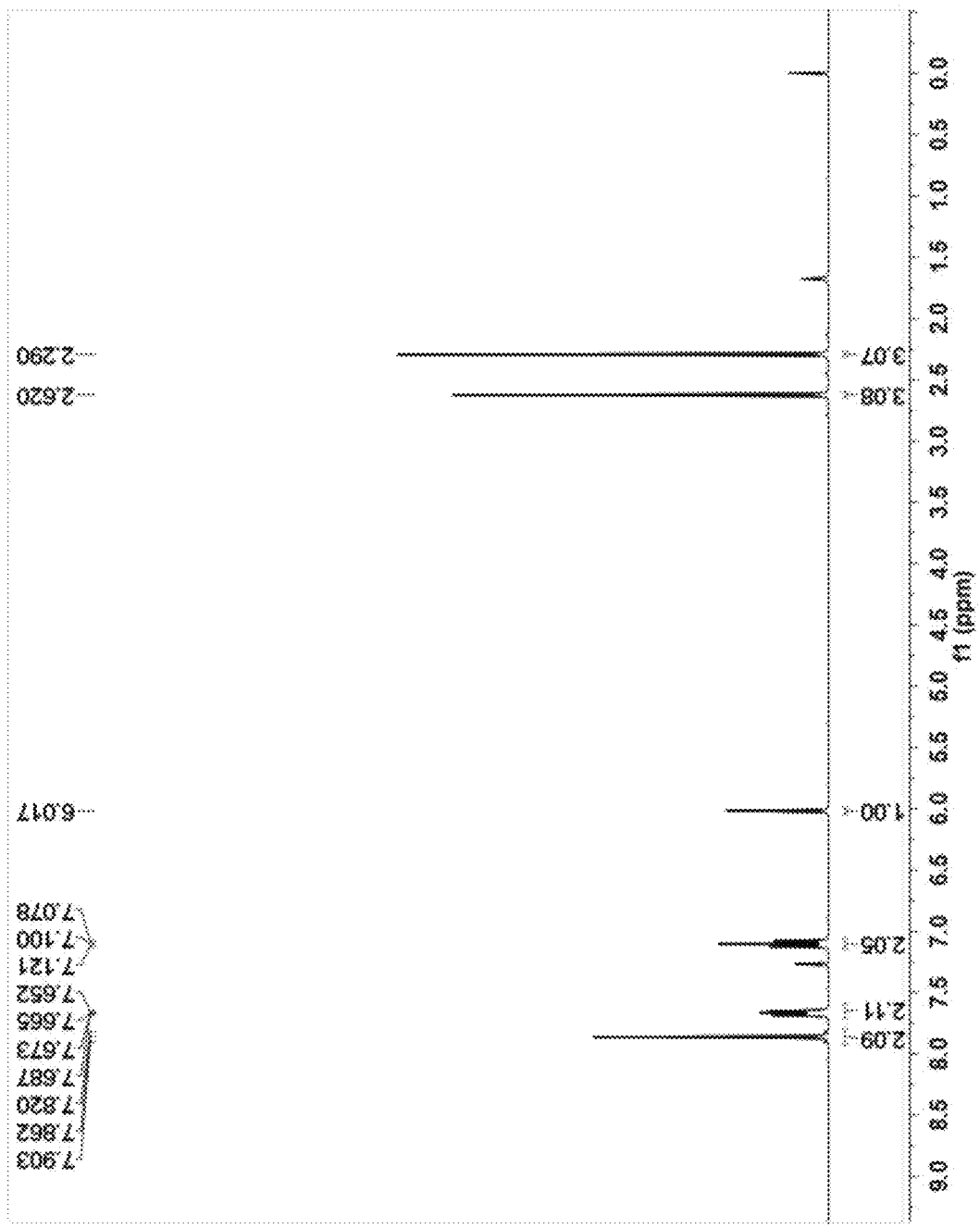
FIG. 3 is a H-spectrum of a compound Ia prepared according to Example 1.

Into a dry reaction flask were weighed a metal catalyst Yb(OTf)$_3$ (0.02 mol), a chiral ligand L-PiMe$_2$ (0.02 mol), p-fluorocinnamoyl-3,5-dimethylpyrazole (0.2 mol) sequentially. The flask was replaced with nitrogen for 3 times. 300 mL of dichloromethane was added to activate at 35° C. for 20 min. A monoamide (0.2 mol) and Et$_3$N (0.2 mol) were sequentially added to react at 30-50° C. for 60-80 hours, a the reaction solution was washed with dilute hydrochloric acid, concentrated to dryness, and crystallized with petroleum ether/ethyl acetate to obtain 51 g of catalysate with a yield of 87%. The HPLC purity of the product was 94.65%, the ee was 99.12%, and the HPLC spectrum of the product was shoes in FIG. 2.

Examples 3-10 were experimental data obtained by operating according to the same method as that of Example 1:

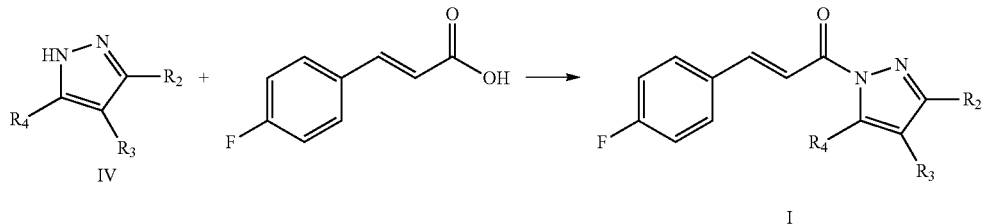

| Example | R₂ | R₃ | R₄ | Organic base | Dehydrant | Solvent | Yield |
|---|---|---|---|---|---|---|---|
| 3 | Me | H | Me | N-methylmorpholine | HATU | THF | 92.2% |
| 4 | Me | H | Me | N-methylmorpholine | DCC | toluene | 91.7% |
| 5 | Me | Ph | Me | triethylamine | EDCI | dichloromethane | 90.7% |
| 6 | Et | H | Me | triethylamine | EDCI | dichloromethane | 89.0% |
| 7 | Ph | H | Me | diethylaniline | PyBOP | hexane | 80.5% |
| 8 | 4-Me—Ph | Me | Ph | diethylaniline | HATU | ethyl acetate | 76.3% |
| 9 | Pr | 3-Et—Ph | Me | DBU | EDCI | tetrahydrofuran | 70.1% |
| 10 | H | H | H | N-methylmorpholine | EDCI | dichloromethane | 90.3% |

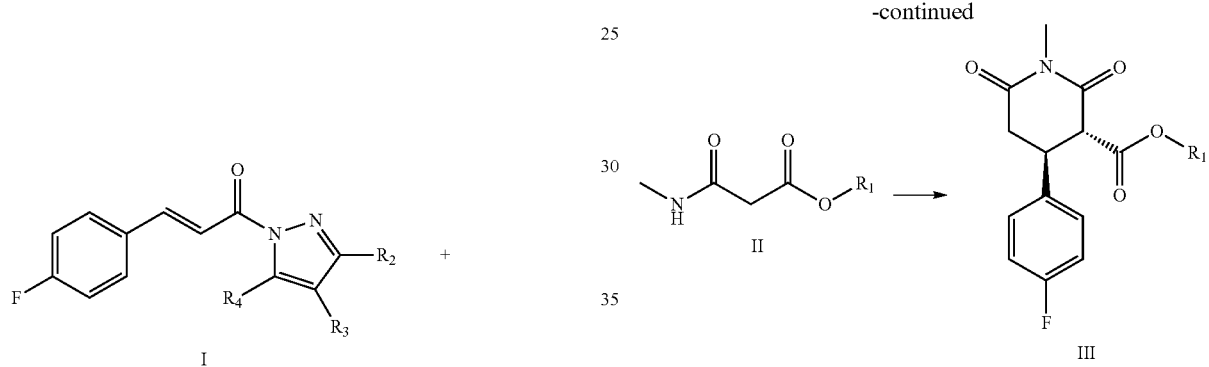

Examples 11-18 were experimental data obtained by operating according to the same method as that of Example 2:

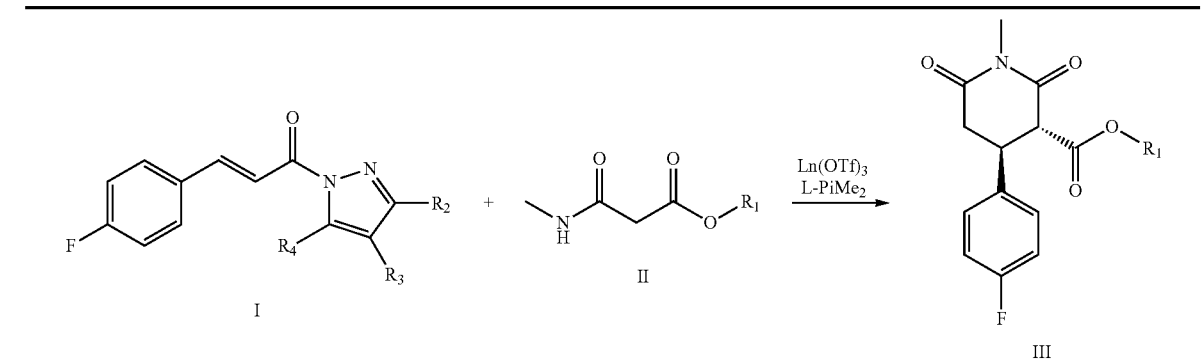

| Example | R1 | R₂ | R₃ | R₄ | Ln | Base | Solvent | Yield | ee |
|---|---|---|---|---|---|---|---|---|---|
| 11 | Me | Me | H | Me | Yb | tri-n-propylamine | THF | 83.4% | 98.89% |
| 12 | Et | Me | H | Me | Yb | Et₃N | toluene | 85.5% | 99.06% |
| 13 | Pr | Me | Ph | Me | Yb | DBU | dichloromethane | 83.9% | 98.79% |
| 14 | i-Pr | Et | H | Me | Yb | Et₃N | dichloromethane | 84.8% | 98.86% |
| 15 | n-Bu | Ph | H | Me | Gd | dimethylaniline | hexane | 80.0% | 97.26% |
| 16 | Et | 4-Me—Ph | Me | Ph | Gd | Et₃N | ethyl acetate | 83.3% | 97.58% |
| 17 | Et | Pr | 3-Et—Ph | Me | Ho | Et₃N | tetrahydrofuran | 80.7% | 97.40% |
| 18 | Me | H | H | H | Er | Et₃N | dichloromethane | 80.6% | 97.61% |

Examples 19-27 were experimental data obtained by operating according to the same method as that of Example 2 except that a different catalyst L was selected:

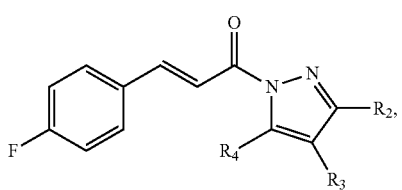

| Example | n | R | Yield (%) | HPLC (%) | ee (%) |
|---|---|---|---|---|---|
| 19 | 1 | Ph— | 82.2 | 90.87 | 98.3 |
| 20 | 1 | 2,6-Me$_2$C$_6$H$_3$— | 85.3 | 94.61 | 98.7 |
| 21 | 1 | 2,6-Et$_2$C$_6$H$_3$— | 84.1 | 94.30 | 98.5 |
| 22 | 1 | 2,6-iPr$_2$C$_6$H$_3$— | 83.7 | 92.15 | 97.9 |
| 23 | 1 | Ph$_2$CH— | 80.8 | 92.54 | 97.7 |
| 24 | 2 | Ph— | 83.1 | 90.60 | 97.1 |
| 25 | 2 | 2,6-Et$_2$C$_6$H$_3$— | 84.3 | 94.13 | 98.6 |
| 26 | 2 | 2,6-iPr$_2$C$_6$H$_3$— | 82.6 | 93.42 | 98.4 |
| 27 | 2 | Ph$_2$CH— | 80.5 | 92.10 | 97.8 |

The invention claimed is:

1. A compound having the structure of formula I:

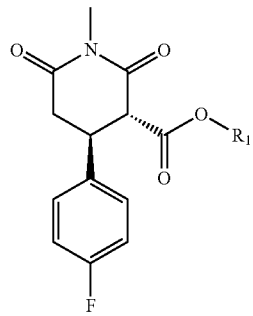

wherein $R_2$, $R_3$ and $R_4$ are each independently $C_1$-$C_6$ alkyl or $C_6$-$C_{10}$ aryl.

2. The compound according to claim 1, wherein the compound has the following structure:

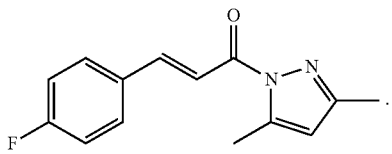

3. A method of preparing a compound of formula III below,

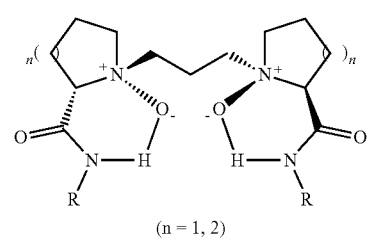

obtained by reacting a compound of formula I with a compound of formula II in the presence of an organic base under the catalysis of a complex formed from a chiral amine oxide L and a rare-earth metal compound Ln(OTf)$_3$:

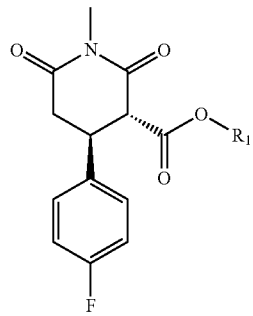

wherein $R_1$ is alkyl, phenyl or benzyl, preferably $C_1$-$C_6$ alkyl, phenyl or benzyl;

$R_2$, $R_3$ and $R_4$ are each independently $C_1$-$C_6$ alkyl or $C_6$-$C_{10}$ aryl;

the chiral amine oxide L has the following structure:

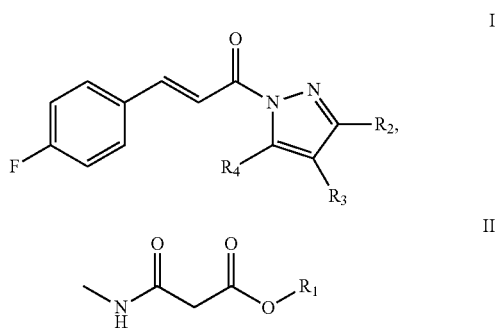

wherein n=1, 2; and R=Ph—, 2,6-Me$_2$C$_6$H$_3$—, 2,6-Et$_2$C$_6$H$_3$—, 2,6-iPr$_2$C$_6$H$_3$—, Ph$_2$CH—; and Ln in the rare-earth metal compound Ln(OTf)$_3$ represents a lanthanide metal selected from La, Ce, Pr, Nd, Pm, Sm, Eu, Gd, Tb, Dy, Ho, Er, Tm, Yb, Lu.

4. The method according to claim 3, Wherein the organic base is an amine.

5. The method according to claim 3, wherein the Ln(OTf)$_3$ is gadolinium trifluoromethanesulfonate [Gd(OTf)$_3$], holmium trifluoromethanesulfonate [Ho(OTf)$_3$], ytterbium trifluoromethanesulfonate [Yb(OTf)$_3$], erbium trifluoromethanesulfonate [Er(OTf)$_3$].

6. The method according to claim 3, wherein the organic base is triethylamine, diisopropylethylamine, trimethylamine, tri-n-propylamine, tri-n-butylamine, dimethyl aniline, diethylaniline, dimethyl benzylamine, diethyl benzylamine, or 1,8-diazabicyclo[5.4.0]undec-7-ene.

7. The method according to claim 3, wherein the reaction is carried out in a solvent such as pentane, hexane, heptane, dichloroethane, chloroform, toluene, ethylbenzene, isopropyl benzene, tetrahydrofuran, methyl tert-butyl ether, 2-methyltetrahydrofuran, ethyl acetate or isopropyl acetate.

8. A method of preparing a compound of formula I,

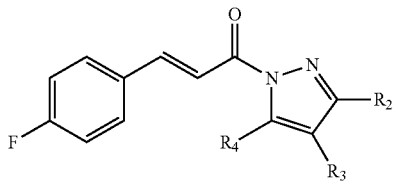

I obtained by condensing a compound of formula IV below with p-fluorocinnamic acid in the presence of a dehydrant and an organic base,

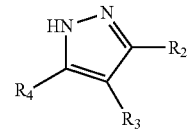

IV wherein $R_2$, $R_3$ and $R_4$ are the same as defined in claim 1.

9. The method according to claim 8, wherein the dehydrant is 1-ethyl-(3-dimethylaminopropyl)carbodiimide hydrochloride, 2-(7-azabenzotriazol)-N,N,N',N'-tetramethyluronium hexafluorophosphate, dicyclohexylcarbodiimide, or benzotriazol-1-yl-oxytripyrrolidinophosphonium hexafluorophosphate.

10. The method according to claim 8, wherein the organic base is N-methylmorpholine, triethylamine, diisopropylethylamine, trimethylamine, tri-n-propylamine, tri-n-butylamine, dimethylaniline, diethylaniline, dimethyl benzylamine, diethyl benzylamine or 1,8-diazabicyclo[5.4.0]undec-7-ene.

* * * * *